(12) United States Patent
Volz et al.

(10) Patent No.: US 9,976,943 B2
(45) Date of Patent: May 22, 2018

(54) DEVICE TO POSITION AND ALIGN A ROTATIONALLY-SYMMETRICAL BODY

(71) Applicant: Helmut Fischer GmbH Institut fur Elektronik und Messtechnik, Sindelfingen (DE)

(72) Inventors: Werner Volz, Sindelfingen (DE); Henry Thiele, Doffingen (DE); Paul Boos, Rottenburg (DE)

(73) Assignee: Helmut Fischer GmbH Institut für Elektronik und Messtechnik, Sindelfingen (DE)

( * ) Notice: Subject to any disclaimer, the term of this patent is extended or adjusted under 35 U.S.C. 154(b) by 234 days.

(21) Appl. No.: 14/703,914

(22) Filed: May 5, 2015

(65) Prior Publication Data
US 2015/0316459 A1    Nov. 5, 2015

(30) Foreign Application Priority Data
May 5, 2014   (DE) .................. 10 2014 106 242

(51) Int. Cl.
*G01N 3/42*   (2006.01)
*G12B 5/00*   (2006.01)

(52) U.S. Cl.
CPC    *G01N 3/42* (2013.01); *G12B 5/00* (2013.01)

(58) Field of Classification Search
CPC .................................. G01N 3/40; G01N 3/42
See application file for complete search history.

(56) References Cited

U.S. PATENT DOCUMENTS

| 4,635,471 A * | 1/1987 | Rogers ..................... G01N 3/42 409/133 |
| 5,639,969 A * | 6/1997 | D'Adamo ................ G01N 3/40 73/790 |
| 2006/0276946 A1* | 12/2006 | Kaneko ..................... G01N 3/48 701/45 |
| 2011/0260720 A1 | 10/2011 | Fischer |

(Continued)

FOREIGN PATENT DOCUMENTS

| DE | 40 22 672 A1 | 1/1992 |
| DE | 100 14 348 A1 | 9/2001 |
| DE | 20 2010 006 062 U1 | 8/2010 |

*Primary Examiner* — Clayton E Laballe
*Assistant Examiner* — Dennis Hancock
(74) *Attorney, Agent, or Firm* — Renner, Otto, Boisselle & Sklar, LLP (57) ABSTRACT

The invention relates to a device to position and align a rotationally-symmetrical body (28) with respect to a measuring device (19) for the implementation of a measurement on the rotationally-symmetrical body (28), having a basic element (24) which has a contact surface (22) on a pin (23) or is allocated to a contact surface (22) on which the rotationally-symmetrical body (28) is supported for the implementation of the measurement, wherein a positioning element (41) which can be moved relative to the contact surface (22) is provided on the basic element (24), said positioning element (41) comprising a prismatic receiver (64), wherein the contact surface (22) is positioned within the prismatic receiver (64) or abuts on this and a movement path of the positioning element (41) towards the basic element (22) corresponds at least to the height of the prismatic receiver (64).

11 Claims, 6 Drawing Sheets

(56) References Cited

U.S. PATENT DOCUMENTS

| | | | | |
|---|---|---|---|---|
| 2012/0166106 A1* | 6/2012 | Niemeyer, III | ...... | A63B 47/008 702/43 |
| 2015/0059481 A1* | 3/2015 | Schaare | ................... | G01N 3/40 73/655 |

* cited by examiner

DEVICE TO POSITION AND ALIGN A ROTATIONALLY-SYMMETRICAL BODY

This application claims priority of Germany Application No. 10 2014 106 242.6 filed May 5, 2014, which is hereby incorporated herein by reference.

The invention relates to a device to position and align a rotationally-symmetrical body with respect to a measuring probe for the implementation of a measurement on the body.

BACKGROUND

To receive rotationally-symmetrical bodies, such as, for example, shafts, the use of measurement prisms is known using which the position of the rotationally-symmetrical body which is supported thereon is fixed. Such a measurement prism has two surfaces which are aligned with respect to each other at a certain angle and which are attached to each other in a V-shape, whereby a rotationally-symmetrical body, such as, for example, a shaft, abuts on each of the two surfaces tangentially. Such measurement prisms indeed enable the position of a rotationally-symmetrical body to be fixed with regard to the measurement prism, though an exact positioning of the rotationally-symmetrical body with respect to a measuring device is not possible in this way. In particular, a measuring point on the rotationally-symmetrical body varies depending on the diameter of the rotationally-symmetrical body.

During a hardness measurement of surfaces on rotationally-symmetrical bodies, such as, for example, lacquer layers, galvanic layers, hard material layers, polymers or uncoated sheet material surfaces or similar, hardness measuring devices are used such as, for example, a "FISCHERSCOPE HM2000 S". Such a hardness measuring device comprises a stand having a measuring housing in which an indenter is arranged as a part of a measuring device. This indenter is arranged within a contact surface of a pin. A planar material is applied to the contact surface and is pressed onto the contact surface by means of a pressing piece of the stand in order to carry out the measurement. The indenter is thus loaded with a predetermined force and penetrates the body. In the case of rotationally-symmetrical bodies, this can be supported on the contact surface, yet cannot be aligned exactly with respect to the indenter with a high level of repeat accuracy, such that the indenter penetrates at the highest or lowest point of the shell surface, perpendicularly to the axis of the rotational body, due to which a measurement has errors.

SUMMARY OF THE INVENTION

The invention provides a device to position and align rotationally-symmetrical bodies with respect to a measuring device which enables such a rotationally-symmetrical body to be positioned and aligned reliably and exactly with respect to the measuring device, independently of different diameters.

This object is solved by a device to position and align a rotationally-symmetrical body which comprises a basic element having a contact surface on which a positioning element which is able to be moved relative to the contact surface is provided which comprises a prismatic receiver, wherein a pin having the contact surface is positioned within the prismatic receiver or abutting onto this and a movement path of the positioning element with respect to the contact surface of the pin on the basic element corresponds at least to the height of the prismatic receiver. Due to this receiver, it is enabled that the rotationally-symmetrical body is fixed in position with respect to the positioning element by the prismatic receiver, wherein the positing element is able to be moved in a defined travelling movement with respect to the contact surface, such that the rotationally-symmetrical body comes to rest on the contact surface independently of the movement path between the positioning element and the basic element and independently of the diameter of the rotationally-symmetrical body, and at the same time is fixed in position by the prismatic receiver. Thus, a fixed measuring point or a fixed measuring plane is provided for a measuring device independently of the size or the diameter of the rotationally-symmetrical body, wherein, at the same time, an alignment of the rotationally-symmetrical body with respect to the measuring plane or contact surface is provided by the prismatic receiver. Thus it is enabled that the measurement to be carried out occurs on the rotationally-symmetrical body at the lowest or highest point and thus a high level of measuring quality is provided due to the repeat accuracy.

In this device, it is preferably provided that the prismatic receiver of the positioning element comprises a through-bore within which the pin extends and a longitudinal axis of the pin [lacuna] on the basic element in an intersection between the surfaces or surface sections of the prismatic receiver which are allocated to each other. Thus not only is the axis of the rotationally-symmetrical body intersected with the axis of the pin, but additionally a fixed measuring point results with respect to the contact surface, independently of the diameter of the rotationally-symmetrical body.

A further preferred embodiment of the device provides that the positioning element is guided through the through-bore along the pin on the basic element during a movement with respect to the basic element or onto the basic element. This enables a simple and compact construction. Preferably, a guiding between the pin of the basic element and the through-bore of the positioning element is provided without clearance. Alternatively or additionally, separate pins can be introduced between the positioning element and the basic element which serve to guide, such that the positioning element is, for example, pins which are inserted relatively fixedly in the basic element. This arrangement can also be exchanged.

The positioning element is preferably held by a sprung mounting in an initial position with respect to the basic element in which the contact surface of the pin is positioned outside the prismatic receiver or abutting onto this. Thus, this device can always be ready for use and reverts to the initial position after the implementation of a measurement in which the positioning element is brought onto the basic element by means of the rotationally-symmetrical body. If a measuring device is provided within the pin, this serves at the same time as protection of a measuring probe or probe tip of the measuring device arranged therein.

The sprung position in particular comprises a flange bushing which abuts on a shoulder of the positioning element and extends in the direction of the basic element, as well as a fastening element which abuts on a shoulder of the basic element and is connected to the flange bushing, wherein a compression spring element is provided between the positioning element and the basic element. Thus a constructively simple construction can be created, having a predetermined and preferably adjustable stroke path between the positioning element and the basic element. At the same time, due to the flange bushing, a guiding or an additional guiding of the positioning element relative to the basic element can occur. Preferably, a compression spring element is arranged coaxially with respect to the flange bushing such that this is guided at the same time.

The prismatic receiver on the positioning element can be formed by two flat surfaces arranged at an angle to each other, by several strip-shaped surface sections which are allocated to one another or by two convexly curved surfaces which are arranged with respect to each other. Independently of the embodiment, a rotationally-symmetrical body abuts tangentially onto each of the surfaces or surface sections and is positioned centrally with respect to the prismatic receiver.

A further advantageous embodiment provides that a respective through-bore is provided on the basic element and the positioning element which are aligned congruently to each other and are provided to receive a fixing means for preferably releasable fixing on a measuring device. Thus it is enabled that this device is able to be arranged on the measuring device to be exchangeable. An upgrading is also possible. Thus it is also enabled that, depending on the measuring task or the geometry of the body to be checked, a corresponding receiving device can be used to position and align the body to be checked on the measuring device.

Furthermore, the basic element can have at least one fixing bore for the preferably releasable fixing in the measurement device. Depending on the accessibility, the fixing of this device can engage from below so directly on the basic element or can occur from above so above the positioning element.

When using this device in a hardness measuring device, it is preferably provided that a measuring probe of the measuring device is able to be arranged in the through-bore of the pin in the basic element. For example, this can be an indenter. Thus this measuring probe is arranged with the longitudinal axis thereof in the longitudinal axis of the pin in order to maintain a fixed measuring point with respect to the contact surface and to the intersection of the two V-shaped surfaces or surface sections of the prismatic receiver.

BRIEF DESCRIPTION OF THE DRAWINGS

The invention as well as further advantageous embodiments and developments of the same are described and explained in more detail below with the aid of the examples depicted in the drawings. The features to be gleaned from the description and the drawings can be applied individually or together in any combination according to the invention. Here are shown.

DETAILED DESCRIPTION

Figure 1:
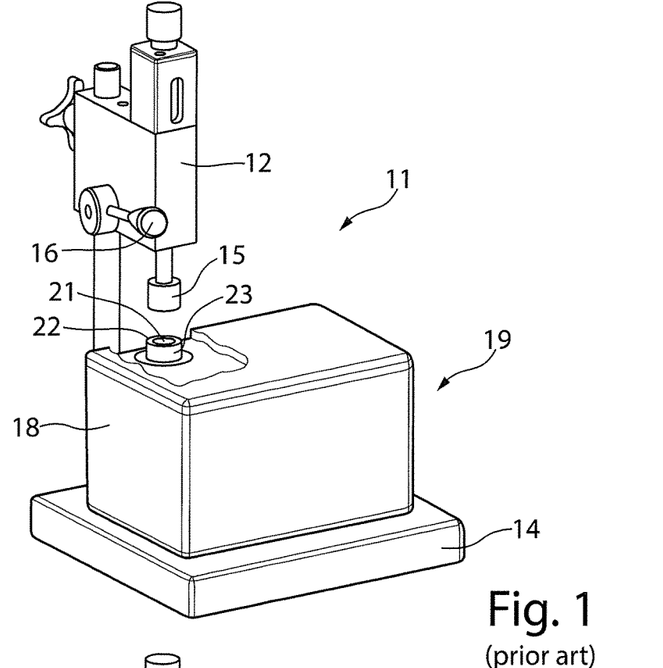
FIG. 1 a perspective view of a hardness measuring device according to prior art, FIG. 2 a perspective view of the hardness measuring device according to FIG. 1, having the device according to the invention, FIG. 3 an exploded depiction of the device according to the invention, FIG. 4 a schematic view from above onto the device according to FIG. 3, FIG. 5 a schematic sectional view along the line V-V in FIG. 4, FIG. 6 a schematic sectional view along the line VI-VI in FIG. 4, FIG. 7 a schematic side view of the device according to FIG. 3 having rotationally-symmetrical bodies which differ in diameter, FIG. 8 a schematic sectional view of an alternative embodiment of a prismatic receiver, FIG. 9a a schematic sectional view of an alternative embodiment to FIG. 2 of the device according to the invention, FIG. 9b a further schematic side view having a partial section according to the embodiment in FIG. 9a, FIG. 9c a schematically enlarged depiction of the partial section in FIG. 9b, and FIGS. 10a to 10d different views of a further alternative use to FIG. 2 of the device according to the invention.

In FIG. 1, a hardness measuring device 11 is depicted perspectively, which is distributed under the reference "FISCHERSCOPE HM2000 S". This hardness measuring device 11 comprises a measuring stand 12 having a socket 14 and a pressing piece 15 which is able to be lowered, said measuring stand 12 being able to be lowered by means of an operating lever 16. A housing 18 having a measurement device 19 is arranged on the socket 14, from which a measuring probe 21 or the tip thereof is visible. This measuring probe 21 is surrounded by a contact surface 22 on a pin 23 of a basic element 24 which is fixed releasably to the housing 18. The measuring probe 21 is an indenter which is pressed in after a flat measurement object is laid on the contact surface 22 and the measurement object is held down onto the contact surface 22 by means of the pressing piece 15 with a predetermined force into the surface of the object to be checked. This occurs due to a force generation device of the measuring device 19 in the housing 18 which is not depicted in more detail. The penetration depth is determined via a displacement measuring system of the measuring device 19 which is also not depicted, from which the relevant hardness value is determined with a data processing device which is not depicted in more detail, in connection with the geometry of the penetration body of the indenter. From this, further material sizes can be determined and emitted.

Figure 2:
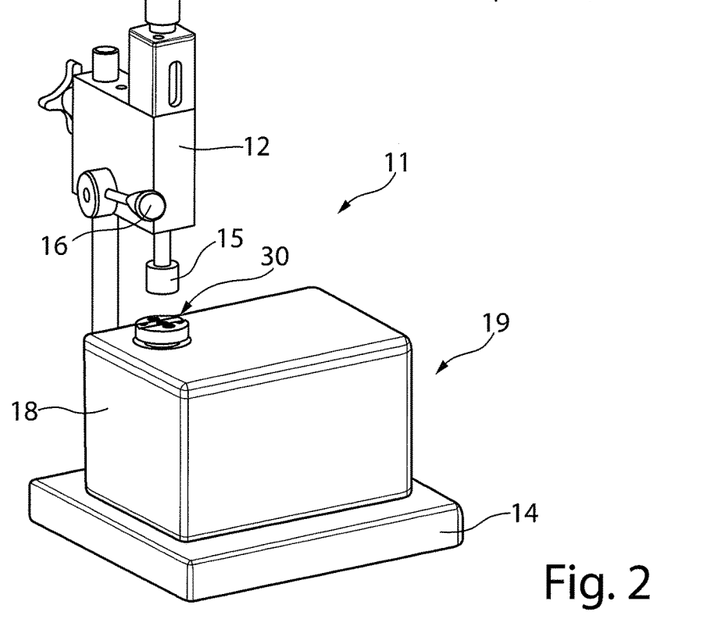
Figure 4:
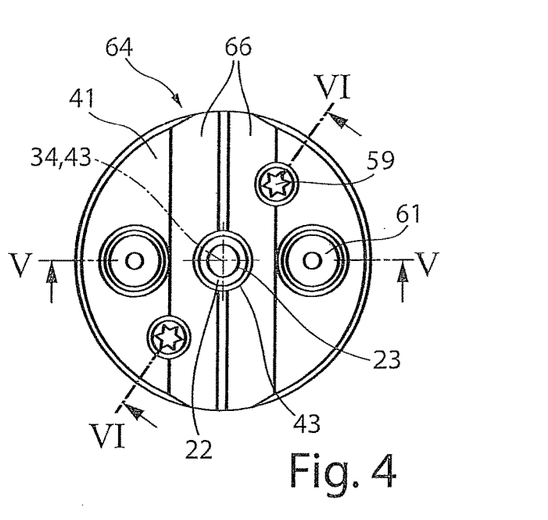

The hardness measuring device 11 according to FIG. 1 is depicted in FIG. 2, in which a device 30 according to the invention to position and align the rotationally-symmetrical body 28 with respect to the measuring probe 21 of the measuring device 19 is provided for the measurement of rotationally-symmetrical bodies 28 (see FIG. 4). This device according to the invention 30 is described in more detail below in FIGS. 3 to 6.

Figure 3:
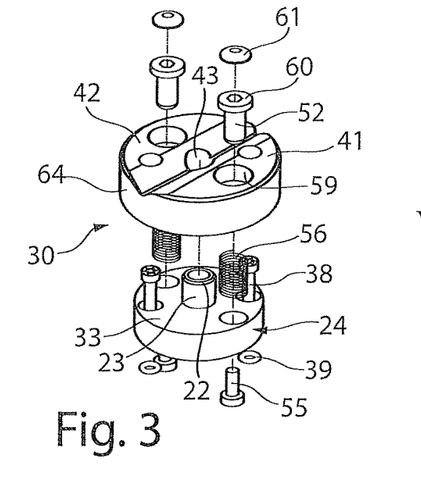
Figure 5:
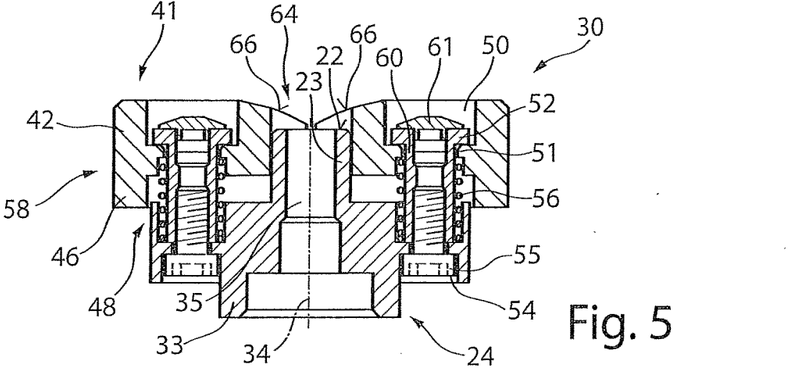
Figure 6:
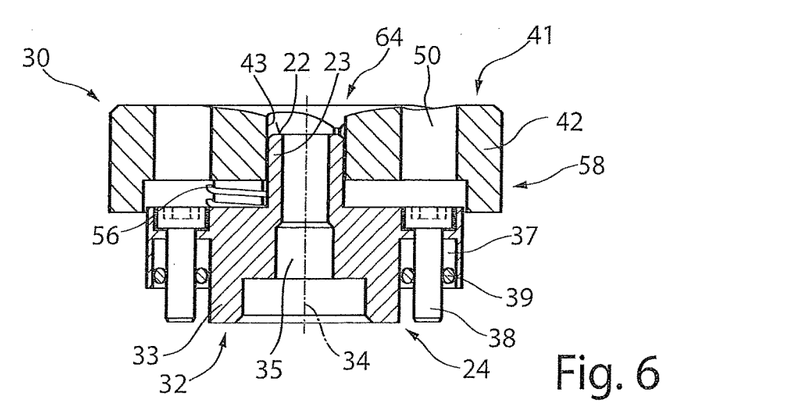

In FIG. 3, an exploded depiction of the device 30 is depicted. From this, the individual components of this device 30 according to the invention arise. FIG. 4 shows a top view 5 and FIGS. 5 and 6 each show a sectional view of the device 30 according to FIG. 4.

This device 30 comprises a basic element 24 which can be formed, for example, as a rotationally-symmetrical part, in particular a milling or rotational part. This comprises a disc-shaped base body 33 on which the pin 23 is arranged in a protruding manner, on the front side of which the contact surface 22 is formed. This pin 23 is provided in a fixed manner and preferably in the longitudinal central axis 34 of the basic element 24. A through-bore 35 extends along the longitudinal central axis 34 in the pin 23, said through-bore 35 being able to be formed to be stepped, for example. The measuring probe 21 can be arranged and/or fixed within this through-bore 35. The basic element 24 furthermore has through-bores 37 into which fixing screws 38 are able to be inserted, such that the device 30 is able to be fixed via these fixing screws 38, for example on the housing 18 of the measuring device 19. Advantageously, an O-ring 39 is provided on each fixing screw 38 such that these cannot fall out of the bores 37.

A positioning element 41 is allocated to the basic element 24. This positioning element 41 advantageously has a disc-shaped base body 42. Preferably, a central through-bore 43 is provided for the positioning of the positioning element 41 with respect to the basic element 24, said through-bore surrounding the pin 23, wherein a fit is advantageously provided between the through-bore 43 and the pin 23, such that the positioning element 41 is mounted centrally and, in particular, without clearance with respect to the basic element 24. Alternatively or additionally, further guiding elements can be provided. In a simple form, dowels can be provided in the basic element 24 or positioning element 41 which are mounted in and guided into corresponding bores. The through-bore 43 is preferably arranged centrally relative to the longitudinal central axis 44 of the positioning element 42.

The positioning element 41 has a annular collar 46 pointing towards the basic element 24 which surrounds an outer periphery of the basic element 24. Thus, an additional tilt-free guiding of the positioning element 41, which can be moved relative to the basic element 24, is enabled. The positioning element 41 is positioned with respect to the basic element 24 by a sprung mounting 48. A flange bushing 52 engages with a bore 50 of the positioning element 41 on a shoulder 51, said flange bushing 52 extending in the direction of the basic element 24. A further bore 54 is provided in the basic element 24 aligned to the bore 50, in which a fixing means, in particular fixing screws 55, is able to be inserted, and engages with the flange bushing 52. A compression spring 56 is provided between the basic element 24 and the positioning element 41 which positions the positioning element 41 in an initial position 58 with respect to the basic element 24. The compression spring 56 is preferably arranged coaxially with respect to the flange bushing 52. A cap 61 is preferably arranged on a head 60 of the flange bushing 52 in order to prevent an operation of the flange bushing 52 to release the screw connection with the fixing screw 55.

The positioning element 41 furthermore comprises a prismatic receiver 64 which is formed by two surfaces 66 which are allocated to each other according to the first exemplary embodiment. These surfaces 66 are, for example, convexly curved. Alternatively, these surfaces 66 can also be formed to be flat. The lines of intersection of the two surfaces 66 cross the longitudinal central axis 34 of the through-bore 35 or the longitudinal central axis 34 of the through-bore 43, wherein the longitudinal central axis 44 and the longitudinal central axis 43 lie within each other and preferably form the longitudinal central axis of the basic element 24 and the positioning element 41.

The positioning element 41 with its receiver 64 is positioned in an initial position 58 in such a way with respect to the contact surface 22 on the basic element 24 such that this lies in the intersection point of the surfaces 66 of the prismatic receiver 64 or outside the receiver 64. Thus the contact surface 22 is protected as a fixed measuring surface. This also applies for a measuring probe 21 of a measuring device which is, if necessary, inserted in the through-bore 35 of the basic element 24.

Figure 7:
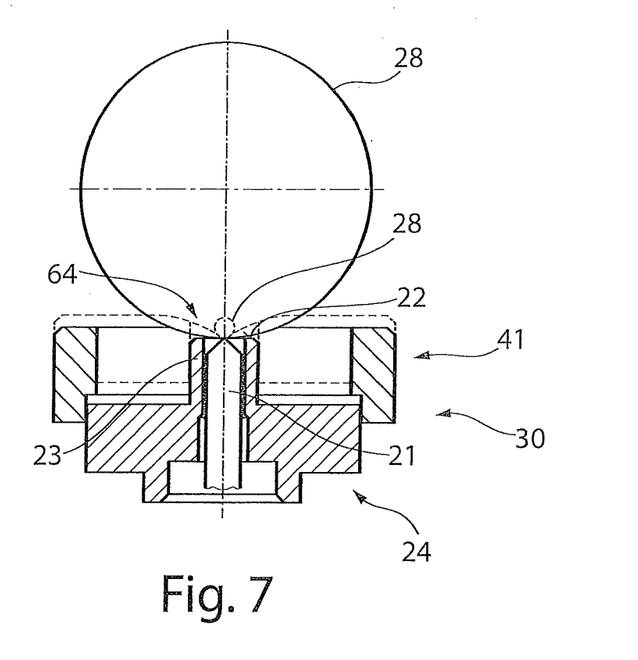

In FIG. 7, a schematic side view of the device 30 having two rotationally-symmetrical bodies 28 which are formed to be of different sizes in cross-section is depicted in order to demonstrate that a fixed measuring point for the measuring probe 21 is provided in the pin 24, on the one hand due to the contact surface 22, independently of the cross-section or of the diameter of the rotationally-symmetrical body 28, and on the other hand by means of the positioning element 41, independently of the allocation of the prismatic receiver 64. Due to the different size or diameter of the rotationally-symmetrical body 28, only the movement path of the positioning element 41 from the initial position 58 in the direction of the basic element 24 is changed. However, in both cases, the rotationally-symmetrical body 28 on the one hand comes to rest on the contact surface 22 and on the other hand remains at the same time fixed in position in the prismatic receiver 64. Thus, the measurement can be carried out at the apex of the rotationally-symmetrical body 28.

Figure 8:
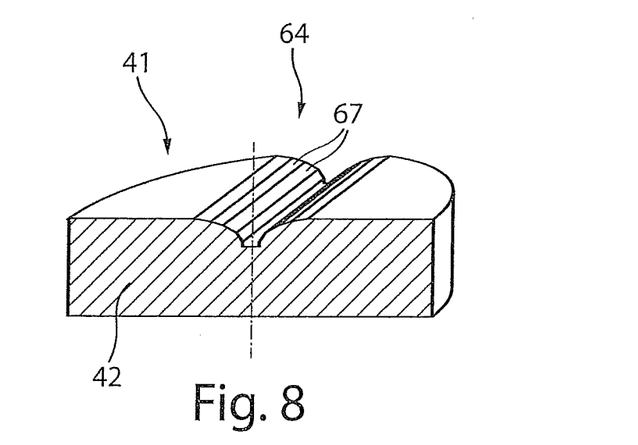

In FIG. 8, an alternative embodiment of the prismatic receiver 64 is depicted. The surfaces 66 which are allocated to each other are, for example, formed by strip-shaped surface sections 67 which are arranged in rows next to one another, each at angles which deviate from one another. Thus, an exact alignment of the rotationally-symmetrical body 28 can also be enabled.

Figure 9A:
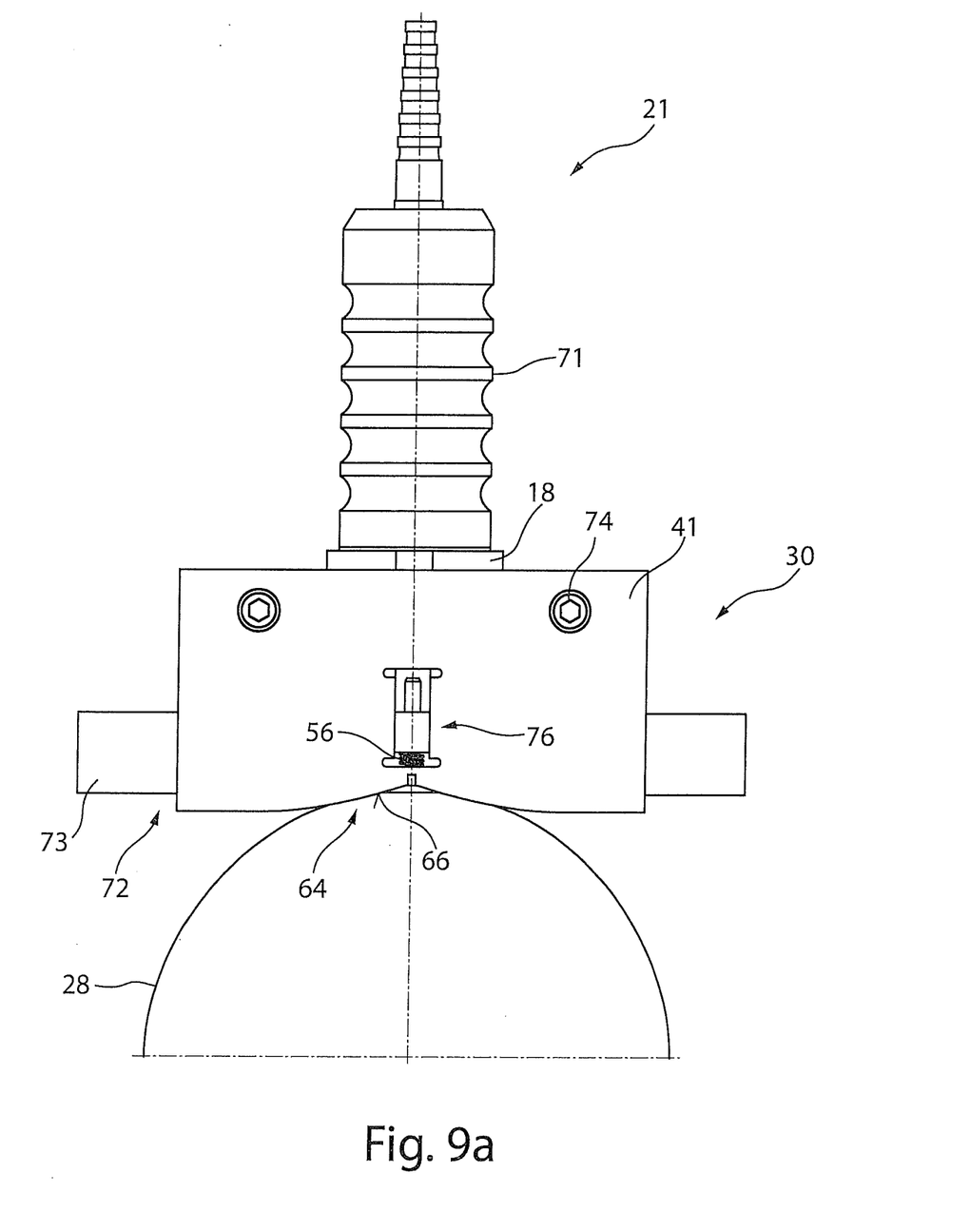
Figures 9B, 9C:
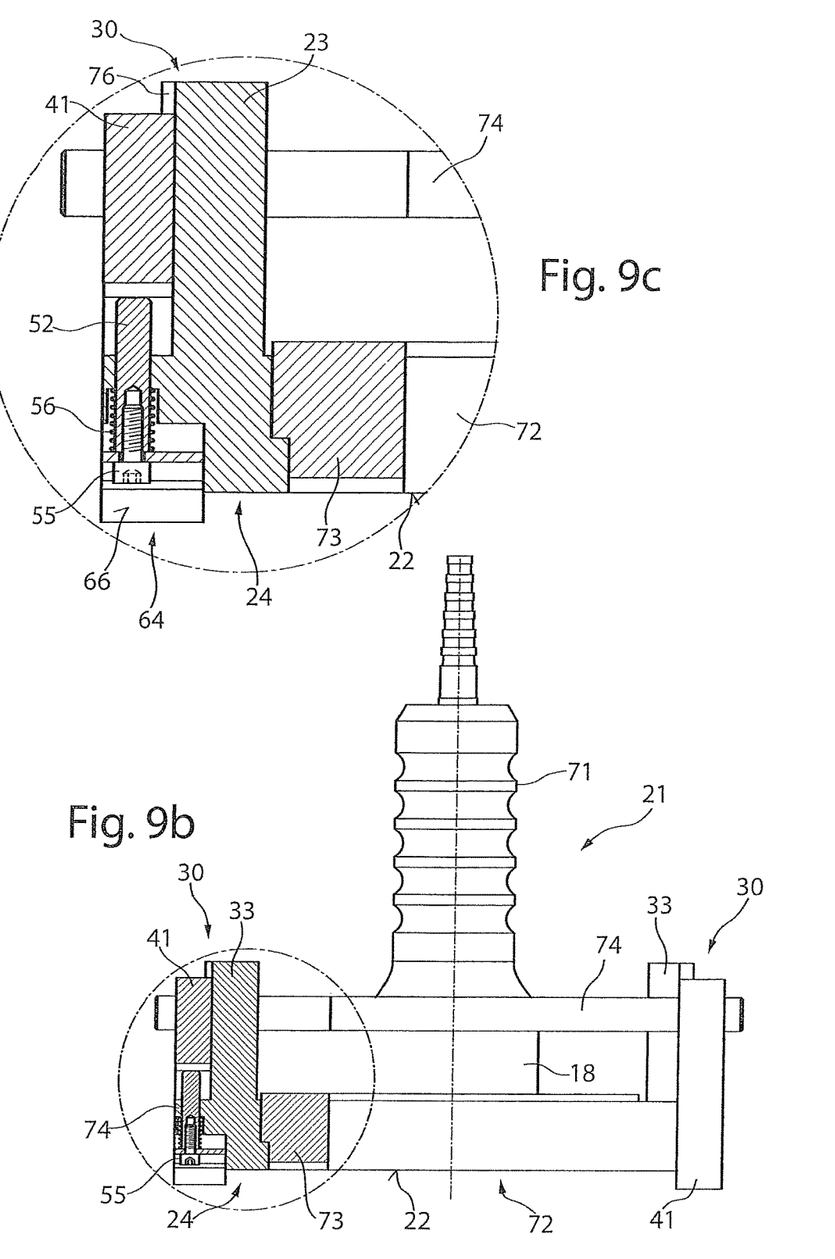

FIG. 9a shows a schematic side view of an alternative embodiment of the device 30 according to the invention. FIG. 9b shows a further side view having a partial section of the device 30 and FIG. 9c shows an enlarged illustration of the partial section in FIG. 9b. The measurement device 19 depicted schematically in FIGS. 9a and 9b comprises a measuring probe 21 which is provided on a housing 18 having a handle 71 to guide the measuring probe 21. The measuring probe 21 has a probe head 72 which has a large diameter compared to the handle 71. At least one coil is provided, for example, in the probe head 72 in order to carry out a layer thickness measurement according to a magnetic-inductive, magnetic method or eddy current method. A Hall sensor may also be provided. The basic element 24 of the device 30 is fixed on the probe head 72. The probe head 72 is formed in this embodiment to be disc-shaped. The basic element 24 is fixed on an annular clamping element 73 which surrounds an outer periphery of the probe head 72 and is able to be clamped on this. The basic element 24 furthermore comprises at least one guiding element 76 instead of a pin 23, which has the same function as the pin 23 according to the embodiment described above. The positioning element 41 is received to be able to be moved along the guiding element 76. Thus the guiding element 76 arranged between the basic element 24 and the positioning element 41 can be provided to be rectangular, dovetail-shaped or similar, such that the positioning element 41 is able to be moved up and down with respect to the contact surface 22 of the measuring probe 21 and to be able to move. The moveable arrangement of the positioning element 41 with respect to the basic element 24 is analogous to the embodiments described above. The positioning element 41 is formed to be planar, which has the prismatic receiver 64 on a lower front side.

The fixing screw 55 is provided within the V-shaped recess of the receiver 64 in order to receive the positioning element 41 to be able to move in a spring-mounted manner with respect to the basic element 24. The two opposing positioning elements 41 are preferably positioned and fixed with respect to each other by fastening elements 74 such as, for example, clamping screws, such that these are both able to be moved in parallel to each other and also perpendicularly to the contact surface 22. When contacting the measuring probe 21 on rotationally-symmetrical bodies 28, such as, for example, pipeline tubes, pipelines (coated, uncoated), water lines or similar, a positioning of the measuring probe 21 occurs via the receiver 64 on the outer periphery of such rotationally-symmetrical bodies 28, wherein by pressing the measuring probe 21 down in the direction of the rotationally-symmetrical body 28, the contact surface 22 in turn follows for connection to the outer periphery of the rotationally-symmetrical body 28, whereby a fixed measuring point is in turn provided. The positioning element 41 must be guided in parallel to the probe head 72, or the positioning element 41 must be aligned perpendicularly to the contact surface 22 of the measuring probe 21.

Figure 10A:
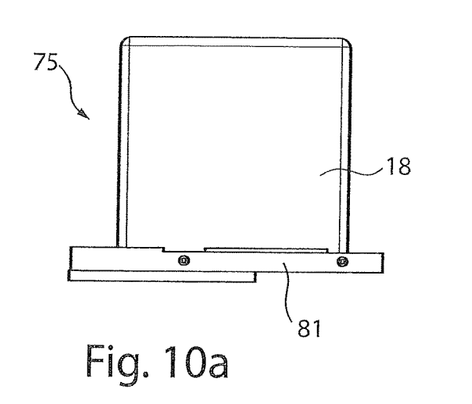
Figure 10B:
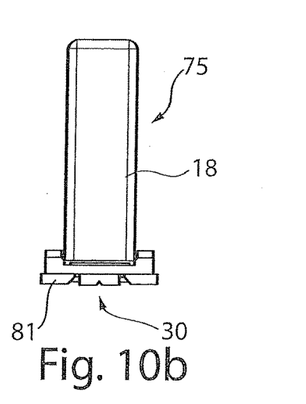

In FIGS. 10a to 10d, a further alternative use of the device 30 according to the invention is depicted. FIGS. 10a and 10b each show a schematic side view of an X-ray fluorescence measurement device 75 which, for example, is formed as a mobile device or a hand-held device. A radiation source for emission of a primary beam as well as a detector for the detection of a secondary beam emitted by a measuring surface is provided, which are not depicted in more detail, in the housing 18 of the X-ray fluorescence measuring device 75. Furthermore, the X-ray fluorescence measuring device 75 comprises an evaluation device with respect to the detected secondary beam.

Figure 10C:
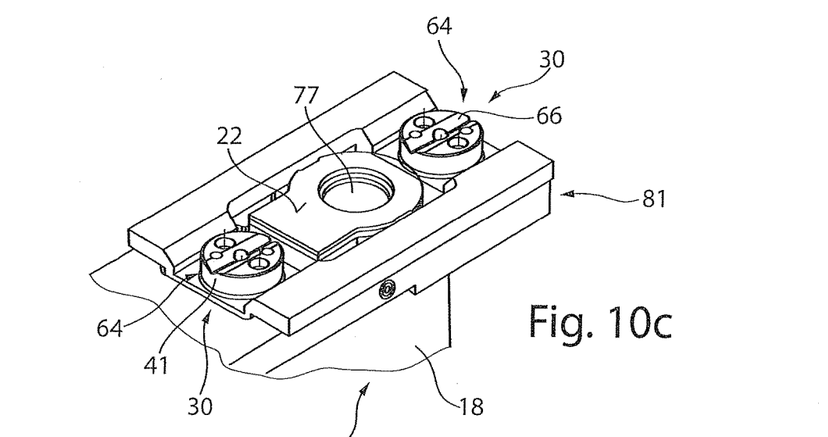

In FIG. 10c, a lower side of the X-ray fluorescence measuring device 75 is depicted which shows an output opening 77 from which the primary beam leaves and a secondary beam which is emitted at the measuring surface can enter the housing 18 again. This output opening 77 is surrounded by a contact surface 22. For the correct positioning of this X-ray fluorescence measuring device 75, at least one device 30 according to the invention is provided adjacent to the output opening 77, wherein, according to the exemplary embodiment in FIG. 10c, a device 30 is arranged on both sides with respect to each contact surface 24.

Figure 10D:
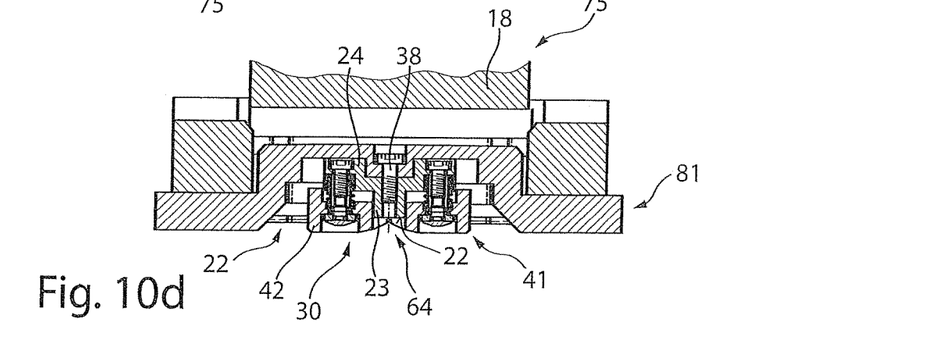

This device 30 can, for example, be mounted on a contact frame 81, as arises in FIG. 10d, or this contact frame 81 can be provided releasably on the housing 18 of the X-ray fluorescence measuring device 75.

In this embodiment it is provided that the contact surface 22 is arranged to abut on the prismatic receiver 64 or outside the positioning element 41, wherein the position or the height of the contact surface 22 corresponds in ratio to the prismatic support 64 according to the exemplary embodiment in FIGS. 3 to 6.

Alternatively or additionally, the device 30 can also be provided with the contact surface 22 on the pin 23, wherein the position of the contact surface 22 on the pin 23 and the measuring plane of the X-ray fluorescence measuring device 75 are then aligned and adjusted to one another.

In addition, a further device 30 can be provided on the housing removed from the output opening 77 as an auxiliary pole, such that the housing 18 of the X-ray fluorescence measuring device 75 is aligned with regard to the entire length thereof with respect to a rotationally-symmetrical body 28.

The invention claimed is:

1. A device to position and align a rotationally-symmetrical body with respect to a measuring device for the implementation of a measurement on the rotationally-symmetrical body, the device comprising:
   a basic element including a pin having a contact surface for supporting the rotationally-symmetrical body to implement the measurement, and
   a positioning element that is movable along an axis relative to the contact surface such that the contact surface moves along a movement path relative to the positioning element, and
   wherein the positioning element has converging surfaces forming a prismatic receiver for engaging the rotationally-symmetrical body at at least three points of contact and thus positioning the rotationally-symmetrical body,
   wherein the contact surface is centrally disposed with respect to the converging surfaces;
   wherein the positioning element is positioned by a sprung mounting in an initial position with respect to the basic element; and
   wherein the sprung mounting comprises a flange bushing which abuts on a shoulder in a bore of the positioning element and extends in the direction of the basic element, a fastening element which abuts on a shoulder of the bore on the basic element and is connected to the flange bushing, and at least one compression spring arranged between the positioning element and the basic element.

2. The device according to claim 1, wherein the positioning element has a through-bore through which the pin extends.

3. The device according to claim 1, wherein the positioning element has a through-bore in which the pin is guided during a movement of the positioning element relative to the contact surface.

4. The device according to claim 1, wherein the converging surfaces are flat or convexly curved.

5. The device according to claim 4, wherein the positioning element has a through-bore in which the pin is guided during a movement of the positioning element relative to the contact surface.

6. The device according to claim 1, wherein a respective through-bore is provided on the basic element and the positioning element, which are arranged congruently with respect to each other and are provided to receive a fixing member for attaching the device to the measuring device.

7. The device according to claim 1, wherein the basic element has at least one through-bore to receive a fastener for fixing the device to the measuring device.

8. The device according to claim 7, wherein the basic element has at least one through-bore to receive a fixing member for fixing the device to the measuring device.

9. A method of positioning a rotationally-symmetrical body, comprising the steps of:
   arranging the device according to claim 1 on a housing of a hardness measuring device, and
   using the device to position the rotationally-symmetrical body.

10. A method of positioning a rotationally-symmetrical body in a measuring plane of an X-ray fluorescence beam of a mobile X-ray fluorescence device, comprising providing the device according to claim 1 on a housing of the mobile X-ray fluorescence device and using the device to position the rotationally-symmetrical body in a measuring plane of the X-ray fluorescence beam.

11. A method of making tactile measurements of the thickness of thin layers on a rotationally-symmetrical body, comprising arranging the device according to claim 1 on a housing of a measuring probe and using the device for the tactile measurement of the thickness of thin layers on the rotationally-symmetrical body.

* * * * *